(12) United States Patent
Gotoh et al.

(10) Patent No.: US 7,713,406 B2
(45) Date of Patent: *May 11, 2010

(54) BIOSENSOR

(75) Inventors: Masao Gotoh, Kanagawa-ken (JP);
Hiroki Mure, Kanagawa-ken (JP);
Hiroshi Shirakawa, Kanagawa-ken (JP)

(73) Assignee: Abbott Diabetes Care Inc., Alameda, CA (US)

(*) Notice: Subject to any disclaimer, the term of this patent is extended or adjusted under 35 U.S.C. 154(b) by 1343 days.

This patent is subject to a terminal disclaimer.

(21) Appl. No.: 11/123,230

(22) Filed: May 6, 2005

(65) Prior Publication Data

US 2005/0258052 A1 Nov. 24, 2005

Related U.S. Application Data

(60) Continuation of application No. 10/303,084, filed on Nov. 25, 2002, now Pat. No. 6,893,545, which is a continuation of application No. 09/664,319, filed on Sep. 18, 2000, now Pat. No. 6,503,381, which is a division of application No. 09/484,539, filed on Jan. 18, 2000, now Pat. No. 6,156,173, which is a continuation of application No. 08/990,997, filed on Dec. 15, 1997, now Pat. No. 6,071,391.

(30) Foreign Application Priority Data

| Sep. 12, 1997 | (JP) | 9-267812 |
| Sep. 12, 1997 | (JP) | 9-267814 |
| Sep. 30, 1997 | (JP) | 9-282642 |
| Sep. 30, 1997 | (JP) | 9-282643 |

(51) Int. Cl.
*G01N 27/327* (2006.01)

(52) U.S. Cl. ............... 205/792; 205/777.5; 204/403.04

(58) Field of Classification Search ........... 204/403.01–403.15; 205/777.5, 778, 792
See application file for complete search history.

(56) References Cited

U.S. PATENT DOCUMENTS

| 4,301,412 A | 11/1981 | Hill et al. |
| 4,301,414 A | 11/1981 | Hill et al. |

(Continued)

FOREIGN PATENT DOCUMENTS

EP 0 120 715 10/1984

(Continued)

OTHER PUBLICATIONS

Caplus abstract of D'Costa (Quinoprotein glucose dehydrogenase and its applicaiotn.in an amperometric glucose sensor, biosensors (1986), 2(2;. 71-87).

*Primary Examiner*—Alex Noguerola
(74) *Attorney, Agent, or Firm*—Edward J. Baba; Bozicevic, Field & Francis LLP

(57) ABSTRACT

A biosensor comprises a space part for sucking and housing a sample formed of two upper and lower plates, the two plates being stuck together by an adhesive layer, the space part for sucking and housing the sample being constituted so as to be partially opened in the peripheral part and partially closed by the adhesive layer, and has a working electrode having at least glucose oxidase immobilized thereon and a counter electrode on the same plane of the plate.

30 Claims, 15 Drawing Sheets

U.S. PATENT DOCUMENTS

| | | | |
|---|---|---|---|
| 4,303,887 A | 12/1981 | Hill et al. | |
| 4,473,457 A | 9/1984 | Columbus | |
| 4,582,684 A | 4/1986 | Vogel et al. | |
| 4,714,874 A | 12/1987 | Morris et al. | 324/444 |
| 4,757,022 A | 7/1988 | Shults et al. | 204/403.05 |
| 4,854,153 A | 8/1989 | Miyagawa et al. | |
| 4,894,137 A | 1/1990 | Takizawa et al. | |
| 4,999,582 A | 3/1991 | Parks et al. | |
| 5,108,564 A | 4/1992 | Szuminsky et al. | |
| 5,120,420 A | 6/1992 | Nankai et al. | |
| 5,128,015 A | 7/1992 | Szuminsky et al. | |
| 5,141,868 A | 8/1992 | Shanks et al. | |
| 5,266,179 A | 11/1993 | Nankai et al. | |
| 5,282,950 A | 2/1994 | Dietze et al. | |
| 5,320,732 A | 6/1994 | Nankai et al. | |
| 5,332,479 A | 7/1994 | Uenoyama et al. | |
| 5,352,351 A | 10/1994 | White et al. | |
| 5,354,447 A | 10/1994 | Uenoyama et al. | |
| 5,384,028 A | 1/1995 | Ito | |
| 5,410,474 A | 4/1995 | Fox | |
| 5,437,999 A | 8/1995 | Diebold et al. | |
| 5,438,271 A | 8/1995 | White et al. | |
| 5,582,697 A | 12/1996 | Ikeda et al. | |
| 5,589,045 A | 12/1996 | Hyodo | |
| 5,650,062 A | 7/1997 | Ikeda et al. | |
| 5,651,869 A | 7/1997 | Yoshioka et al. | |
| 5,682,884 A | 11/1997 | Hill et al. | |
| 5,707,504 A | 1/1998 | Jyouno et al. | |
| 5,759,364 A | 6/1998 | Charlton et al. | |
| 5,837,886 A | 11/1998 | Nakahara et al. | |
| 6,071,391 A | 6/2000 | Gotoh et al. | 204/403 |
| 6,143,164 A | 11/2000 | Heller et al. | 205/777.5 |
| 6,153,069 A | 11/2000 | Pottgen et al. | |
| 6,156,173 A | 12/2000 | Gotoh et al. | 204/403 |
| 6,218,134 B1 | 4/2001 | Yamauchi et al. | 435/7.9 |
| 6,416,641 B1 * | 7/2002 | Ikeda et al. | 204/403.04 |
| 6,503,381 B1 | 1/2003 | Gotoh et al. | 204/403.14 |

FOREIGN PATENT DOCUMENTS

| | | | |
|---|---|---|---|
| JP | 56-79242 | 6/1981 | |
| JP | 59-128443 | 7/1984 | |
| JP | 91-502419 | 10/1986 | |
| JP | 62-136018 | 6/1987 | |
| JP | 63-187150 | 8/1988 | 204/403 |
| JP | 64-57159 | 3/1989 | 204/403 |
| JP | 64-91052 | 4/1989 | 204/403 |
| JP | 1-129155 | 5/1989 | 204/403 |
| JP | 1-287455 | 11/1989 | 204/403 |
| JP | 1-291153 | 11/1989 | |
| JP | 2-120655 | 5/1990 | 204/403 |
| JP | 3-269358 | 11/1991 | |
| JP | 4-340453 | 11/1992 | |
| JP | 4-357449 | 12/1992 | |
| JP | 5-164724 | 6/1993 | |
| JP | 7-55755 | 3/1995 | |
| JP | 7-67058 | 3/1995 | |
| JP | 8-502589 | 3/1996 | |
| JP | 8-114571 | 5/1996 | |
| JP | 8-128775 | 5/1996 | |
| JP | 8-254521 | 10/1996 | |
| JP | 8-285814 | 11/1996 | |
| JP | 8-327580 | 12/1996 | |
| JP | 9-68512 | 3/1997 | |
| JP | 9-101280 | 4/1997 | |
| JP | 9-159642 | 6/1997 | |
| JP | 9-159644 | 6/1997 | |
| JP | 9-166571 | 6/1997 | |
| JP | 9159642 | 6/1997 | |
| JP | 9-166571 | 9/1997 | |
| JP | 9-264870 | 10/1997 | |
| JP | 9292355 | 11/1997 | |
| JP | 10002874 | 1/1998 | |
| WO | WO86/00138 | 1/1986 | |
| WO | 94/29706 | 12/1994 | |
| WO | 95/22597 | 8/1995 | |
| WO | 01/33216 | 5/2001 | |
| WO | 01/67099 | 9/2001 | |

* cited by examiner

BIOSENSOR

This application is a continuation of U.S. application Ser. No. 10/303,084, filed Nov. 25, 2002, now U.S. Pat. No. 6,893,545, which is a continuation of U.S. application Ser. No. 09/664,319, filed Sep. 18, 2000, now U.S. Pat. No. 6,503,381, which is a divisional of U.S. application Ser. No. 09/484,539, filed Jan. 18, 2000, now U.S. Pat. No. 6,156,173, which is a continuation of U.S. application Ser. No. 08/990,997, filed Dec. 15, 1997, now U.S. Pat. No. 6,071,391. This application also claims foreign priority from the following Japanese applications 09-267812, filed on Sep. 12, 1997; 9-267814, filed on Sep. 12, 1997; 9-282643, filed on Sep. 30, 1997; and 9-282642, filed on Sep. 30, 1997.

BACKGROUND OF THE INVENTION

This invention relates to a biosensor. More specifically, it relates to a glucose biosensor having glucose oxidase immobilized thereon or a biosensor having an oxidoreductase immobilized thereon.

PRIOR ART

In a conventional biosensor having glucose oxidase immobilized on a working electrode, a counter electrode or the counter electrode and a reference electrodes, in addition to the working electrode, are arranged on the same plane of a flat base. In a glucose biosensor having the electrode arrangement as described above, two method are adapted to bring a measuring sample into contact with the working electrode.

The first method, which comprises dropping the measuring sample directly onto the working electrode, has a problem in that much labor and time are required from the sampling to the dropping. The second method involves the use of a structure formed of a spacer having a groove arranged on an electrode base and a cover having an air hole further arranged thereon to provide a sample suction opening part, a cylindrical part for sucking and housing the sample, and an air vent hole part. This method has an advantage that it does not take much labor and time since the measuring sample is directly guided onto the working electrode, but has a disadvantage of requiring a complicated process in element manufacture such as the setting of the sample suction opening part and the air vent hole part on both ends of the cylindrical part.

SUMMARY OF THE INVENTION

One object of this invention is to provide a glucose biosensor having glucose oxidase immobilized thereon.

The other object of this invention is to provide a biosensor easy to manufacture and measure, and thus suitable also as a disposable glucose biosensor.

The glucose biosensor of this invention has a structure requiring no air vent hole part.

In the glucose biosensor having glucose oxidase immobilized on an electrode, the upper and lower parts of a space part for sucking and housing a sample are formed of two upper and lower plates, the two plates are mutually stuck by an adhesive layer, the space part for sucking and housing the sample is constituted so as to be partially opened in the periphery and partially closed by the adhesive layer, and an electrode structure having at least glucose oxidase immobilized thereon is provided on the plate, whereby the manufacture and measurement are facilitated. When the upper and lower plates are tapered, a target sample can be precisely caught, and the roundness of the tip further provides an operational advantage such that the affected part is not damaged, for example, in blood sampling on a finger. This biosensor is thus suitable as a disposable glucose biosensor.

The two plates constituting the space part are stuck together only by an adhesive layer or by a spacer with adhesive on both sides. The two plates are constituted as follows. In the first embodiment, the electrode structure is formed within the same plane on the same base, and this base is stuck to the other plate (cover) through the adhesive layer or the like. In the second embodiment, one electrode is formed on one base, and this base is stuck to the other base having one electrode or two electrodes formed thereon so as to have a facing structure in which the electrodes are mutually opposed on the inside. In both cases, the upper and lower parts of the space part for sucking and housing the sample are formed of two plates, the two plates are mutually stuck by the adhesive layer or the like, the space part for sucking and housing the sample is constituted so as to be partially opened in the peripheral part and partially closed by a thick part such as the adhesive layer, and the electrode structure having at least glucose oxidase immobilized thereon is provided on the plate.

The use of the spacer with adhesive on both sides is given herein as an example to mutually stick the upper and lower plates, but the manufacturing process can be simplified by the use of only the adhesive layer as described below. In a biosensor in which a working electrode having an oxidoreductase immobilized thereon and its counter electrode are arranged so as to have a facing structure, for example, each base having each electrode on the inside is adhered together through the adhesive layer, whereby an inexpensive manufacturing method can be realized.

The biosensor requires a connector having a special structure since lead parts for ensuring electric continuity are mutually opposed in the inner part.

Biosensors which do not require such a connector are described below.

(1) A biosensor which comprises a working electrode and a counter electrode formed on the inside of a longer lower base and a shorter upper base through an adhesive layer or a spacer, respectively, and a lead part for each electrode formed in such a manner that the end part is situated in a position on the lower base never superposed on the upper base, the electrode on the upper base being conducted to its lead part through an adhesive layer or a spacer.

(2) A biosensor which comprises a working electrode and a counter electrode formed on the inside of a longer upper base and a shorter lower base through an adhesive layer or a spacer, respectively, and a lead part for each electrode formed on the surface side of the upper base, the electrode provided on the upper base being conducted to its lead part through the base, and the electrode provided on the lower base being conducted to its lead part provided on the upper base through an adhesive layer or a spacer.

This invention also provides a biosensor device enhanced in reliability of the device, improved in a series of operability up to measurement end, and advantageous in cost by avoiding the operation by the wrong recognition in insertion of a foreign matter other than the sensor.

Such a device comprises an element reaction sensor member to be inserted to the connector part of a device body in such a manner as to be attachable and detachable, the element reaction sensor member having each output terminal of a working electrode and a counter electrode electrically connected to the connector part side input terminals, and an element reaction part formed at least on the working electrode. The element reaction sensor member further has a sensor insertion judging electrode, and the connector part of the device body also has two input terminals with which the sensor insertion judging electrode output terminal makes contact, so that the system of the device body is started by the contact with the two input terminals to judge the sensor insertion by a control part.

BRIEF DESCRIPTION OF THE DRAWINGS

FIG. 10a is a perspective view of one embodiment of the biosensor according to this invention.

FIG. 10b is a disassembled state view of each component in the embodiment of FIG. 10a.

EMBODIMENTS (A) Embodiments of FIGS. 1a to FIG. 5

Figure 1A:
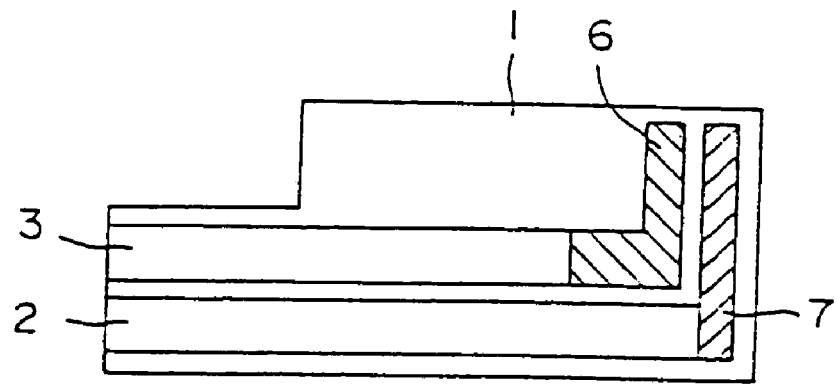
FIGS. 1a, 1b, 1c are plane views of element components used for the manufacture of a glucose biosensor according to this invention.
Figure 1B:
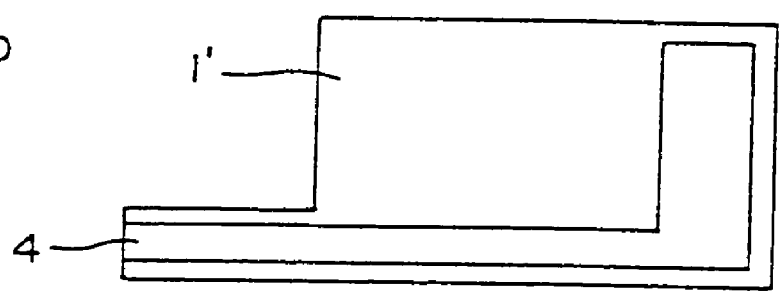
Figure 1C:
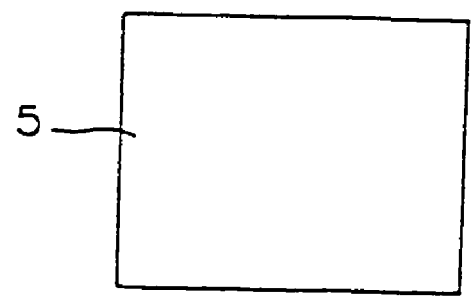
Figure 2:
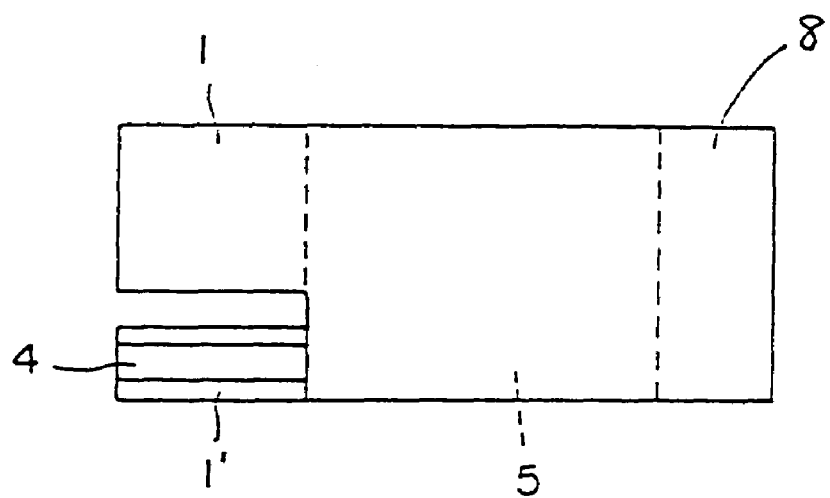
FIG. 2 is a plane view of the assembled glucose biosensor.
Figure 3:
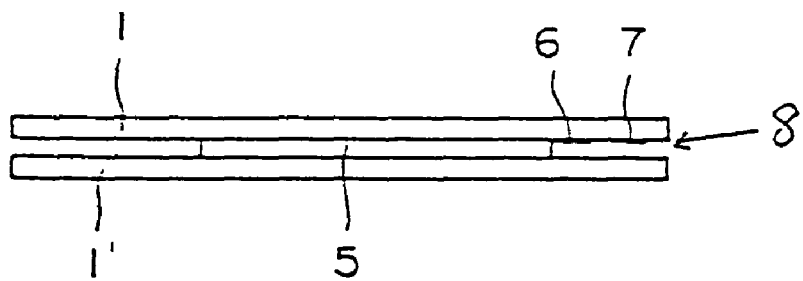
FIG. 3 is a side view of the assembled glucose biosensor.

FIG. 1a shows an element having a working electrode 2 and a reference electrode lead 3 formed on a base 1, and FIG. 1b shows an element having a counter electrode 4 formed on a base 1', and FIG. 1c shows an element component formed of a spacer with adhesive on both sides (about 100-500 µm in thickness) 5(c). FIG. 2 shows a plane view of an element assembled from these components. FIG. 3 shows a side view thereof. The part denoted at 8 in FIGS. 2, 3 is a space part for sucking and housing a sample. The space part 8 is partially opened in the peripheral part, and partially closed by the spacer with adhesive on both sides.

As the base, plastics such as polyethylene terephthalate (PET) and polyvinyl chloride, glass, ceramics, paper, biodegradable material (for example, microorganism producing polyester or the like) are used. The working electrode, the counter electrode and the reference electrode lead are formed from platinum, gold, carbon, palladium or the like by means of screen printing, vapor deposition, sputtering, blocking or the like, and a reference electrode 6 is formed by forming a silver electrode on the reference electrode lead once by screen printing, vapor deposition, sputtering or the like followed by constant current electrolysis or dipping in a ferric chloride aqueous solution, or by applying and laminating silver chloride by screen printing. Although the reference electrode may be set on either of the working electrode-side base and the counter electrode-side base, it is preferably set on the working electrode-side base. A two-electrode structure having no reference electrode is also constituted in the same manner.

Glucose oxidase, which is generally immobilized on a working electrode, may be immobilized on the working electrode periphery, the counter electrode, or the periphery thereof since it is dissolved to an aqueous solution which is a measuring sample, and reacted on the working electrode.

In the immobilization of glucose oxidase, preferably, onto the working electrode, it is formed not only as glucose oxidase single body but also as a mixture layer to which at least one of electron acceptor (mediator) and albumin is added as listed below.

(1) Glucose oxidase layer (2) Glucose oxidase-electron acceptor mixture layer (3) Glucose oxidase-albumin mixture layer (4) Glucose oxidase-electron acceptor-albumin mixture layer The glucose-oxidase layer (1) is formed by dissolving about 1-50 mg, preferably about 5-30 mg of glucose oxidase (GOD), for example, in case of 165800 unit/g GOD, to 1 ml of distilled water or buffer solution, dropping about 0.5-10 µl, preferably about 1-3 µl of the solution (GOD solution) by means of dropping by dispenser or spin coating followed by drying at room temperature to form a layer about 1-200 µm, preferably, about 50-150 µm in thickness.

In the mixture layers (2)-(4), the same method is employed for the formation, except using a GOD aqueous solution having each of the following components added thereto.

Mixture layer (2): Potassium ferricyanide, parabenzoquinone or the like is used as the electron acceptor, and a solution to which about 1-100 mg, preferably about 30-60 mg in potassium ferricyanide, or about 1-200 mg, preferably about 50-150 mg in case of parabenzoquinone is further added is used.

Mixture layer (3): A solution to which about 1-100 mg, preferably about 5-30 mg of bovine serum albumin is added is used.

Mixture layer (4): A solution to which the electron acceptor of the quantity used for the formation of the mixture layer (2) and the bovine serum albumin of the quantity used for the formation of the mixture layer (3) are further added is used.

The added electron acceptor works as described below, and the addition of albumin or the use of buffer solution provides a measurement result with less dispersion to pH change of the measuring solution (glucose aqueous solution).

It is known to indirectly determine glucose concentration by oxidizing glucose under the presence of enzyme by the action of GOD to generate gluconolactone, oxidizing the $H_2O_2$ generated then on the working electrode, and measuring the oxidizing current value at that time. Since the rate of oxidizing reaction is limited by the dissolved oxygen concentration in a liquid concentrate sample in which a measuring solution is not diluted with water, however, the linear calibration range is only shown up to about 100 mg/dl of glucose concentration.

Therefore, instead of the oxygen limited in concentration in solution, the electron acceptor is used together with GOD. When the mediator is potassium ferricyanide $K_3Fe(CN)_6$, the reaction advances as follows.

$$\text{Glucose} + 2\text{Fe(CN)}_6\ldots + \text{H}_2\text{O} \xrightarrow{\text{GOD}}$$
$$\text{gluconic acid} + 2\text{H}^+ + 2\text{Fe(CN)}_6\ldots$$

The ferrocyan ion generated then is oxidized by the working electrode to generate oxidizing current.

$$2\text{Fe(CN)}_6\text{---} \rightarrow 2\text{Fe(CN)}_6\text{---} + 2e-$$

When parabenzoquinone is used instead of potassium ferricyanide as mediator, hydroquinone is generated by the reaction of glucose with parabenzoquinone under the presence of GOD, the generated hydroquinone is oxidized by the working electrode to generate oxidizing current, and its value is measured.

$$\text{hydroquinone} \rightarrow \text{parabenzoquinone} + 2\text{H}^+ + 2e^-$$

On the other hand, although the counter electrode is usable without particularly immobilizing anything thereon, a layer consisting of at least one of albumin and electron acceptor may be formed thereon. In this case, the inclination of concentration apt to be caused in dissolution or dispersion of the mixture layer by the sample solution, which is observed when the mixture layer is provided only on the working electrode, is advantageously eliminated, and the measuring precision is also improved.

In order to smooth the contact of the measuring sample solution with the immobilized GOD, means such as application of a surface active agent such as lecithin, Triton X-100 (Commercial name) or the like onto the working electrode, the counter electrode, the working electrode periphery, the counter electrode periphery, the working electrode and its periphery, or the working electrode and its periphery, or nipping of an impregnation accelerator such as nonwoven fabric or filter paper by utilizing the clearance of the opening part around the space part may be also applied.

A low molecule such as sucrose can be also mixed to the above mixture as a moisture retaining agent, and a cross-linking agent such as glutaraldehyde can be further mixed to the above mixture or bonded onto the electrode to stabilize the immobilization.

The measurement of glucose concentration is performed by bringing about 0.5-10 μl of a glucose aqueous solution having a prescribed concentration into contact with the thus-manufactured glucose biosensor to suck it, applying a voltage of about 0.4-1.2V, preferably about 0.6-1.0V thereto after the reaction for about 1-120 seconds, and measuring the current value, for example, after 20 seconds from the application. A potentiogalvanostat and a function generator are used for the measurement.

Figure 4A:
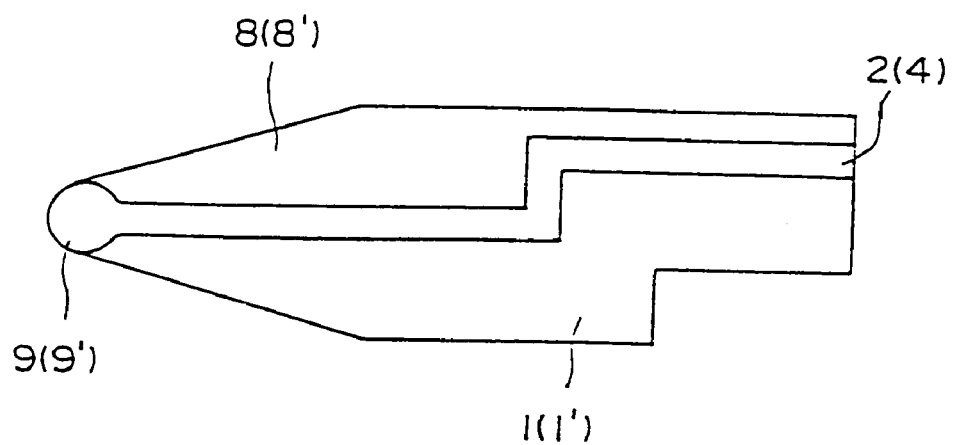
FIGS. 4a, 4b each are plane views of element components used for the manufacture of a preferable glucose biosensor according to this invention.
Figure 4B:
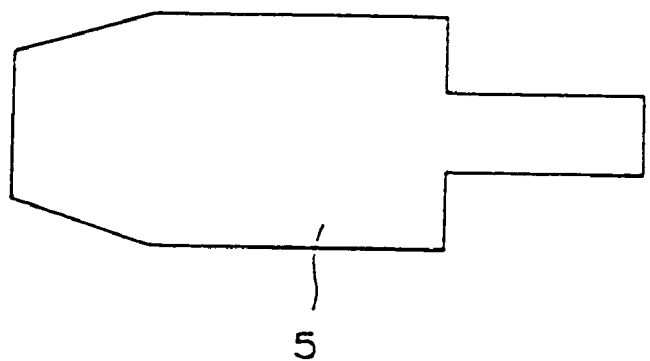

When the glucose biosensor is brought into contact with the glucose aqueous solution, one end side of each base 1 (1') is formed into a tapered part 8 (8') as shown in FIG. 4, and the tip part 9 (9') of the working electrode 2 (or the counter electrode 4) is provided on the tapered part, preferably on the tip thereof. Namely, FIG. 4 shows element components formed of (a) the base 1 (or 1') having the working electrode 2 (or the counter electrode 4) formed thereon, and (b) the spacer with adhesive on both sides 5, and the bases 1, 1' can be integrated together through the spacer 5 with the working electrode 2 side and the counter electrode 4 side of the bases 1, 1' inside. Since the separated electrodes are provided on the base tapered parts in such a sensor, the measuring solution can be directly collected even if it is a trace amount, and the quick contact with the working electrode is thus a great convenience. The side contacting the sample of the base is tapered, whereby the intended sample can be precisely caught. The roundness of the tip also provides an advantage that the affected part is never damaged, for example, in blood sampling on a finger.

The glucose biosensor having glucose oxidase immobilized thereon is constituted as described above, whereby the manufacture and measurement can be facilitated, such a glucose biosensor can be thus used as a disposable biosensor for a liquid concentrate sample as solution sample for domestic medical examination (self-care), particularly self-management of diabetes, and prevention and early detection of diabetes by measurement of blood sugar or urine sugar, and a wide use such as use for glucose management in food manufacturing process can be expected.

EXAMPLE A1

A counter electrode, a working electrode, and a reference electrode lead each of which was made of carbon were formed in a film thickness of 5 μm on a polyethylene terephthalate film (0.25 mm in thickness) by screen printing as the embodiment shown in FIGS. 1-3. A silver paste was printed on the reference electrode lead in a thickness of 5 μm by screen printing followed by baking to form a silver electrode. The silver electrode part was dipped in 0.1M HCl, and silver chloride was formed on the surface by performing a constant current electrolysis for 20 minutes at a current density of 0.6 mA/cm$^2$ to form a silver/silver chloride reference electrode. For this constant current electrolysis, a potentiogalvanostat (manufactured by Hokuto Denko HA501) was used.

Onto the working electrode within each electrode having such a structure, a mixture consisting of 10 mg of glucose oxidase (165800 unit) and 48 mg of potassium ferricyanide dissolved in 1 ml of phosphoric acid buffer solution (pH 7.0) was dropped followed by drying under room temperature condition to manufacture two kinds of glucose biosensors A (using the reference electrode) and B (using no reference electrode).

To the manufactured glucose biosensors, 5 μl of a glucose aqueous solution having a prescribed concentration was introduced from a sample inlet part to advance the reaction for 5 seconds, a voltage of 0.6V is then applied onto the working electrode, and the current value after 20 seconds from the application was measured. A potentiogalvanostat (HA 501) and a function generator (manufactured by Hokuto Denko HB-104) were used for the measurement.

Figure 5:
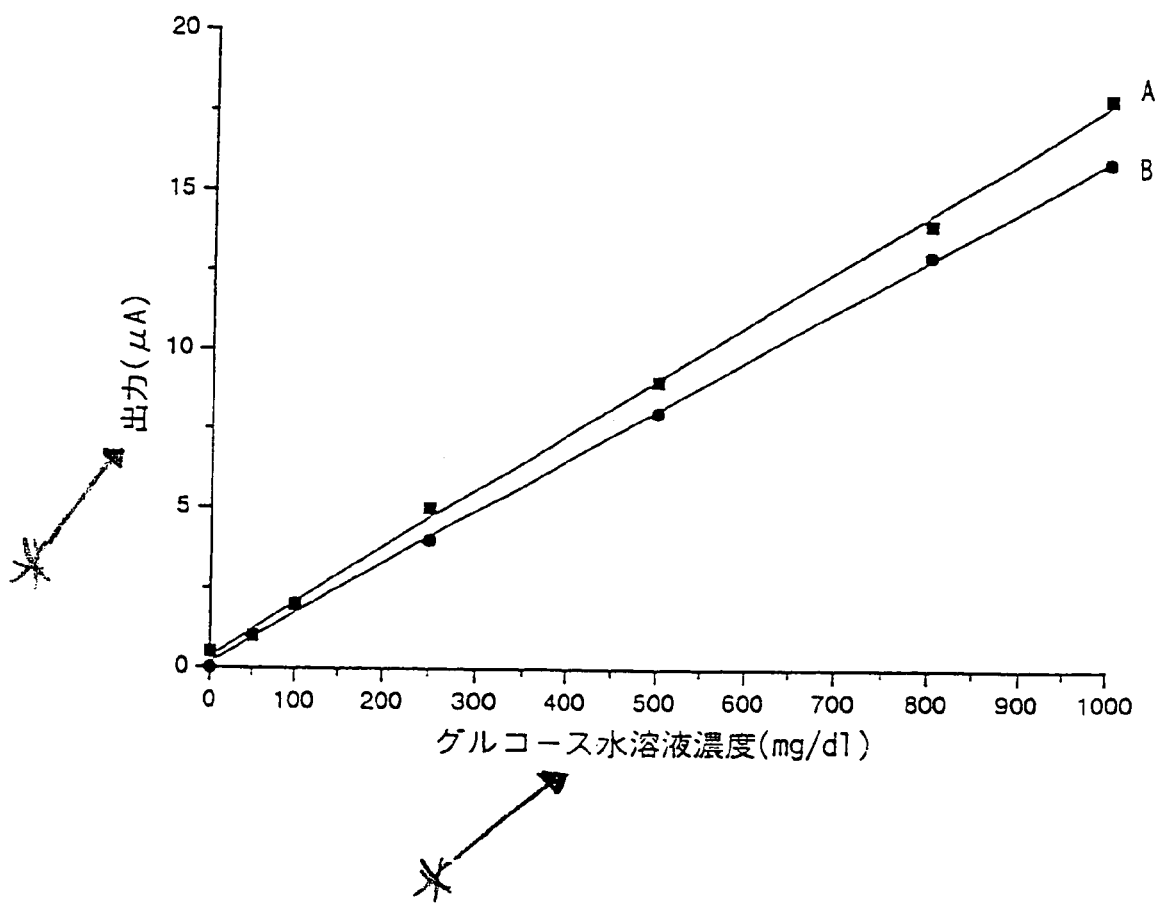
FIG. 5 is a calibration curve graph showing the relation between concentration of glucose aqueous solution and output.

The measurement result (output) is shown in the following table and the graph of FIG. 5.

TABLE

| Glucose concentration (mg/dl) | A | B |
|---|---|---|
| 0 | 0.5 μA | 0 μA |
| 50 | 1 μA | 1 μA |
| 100 | 2 μA | 2 μA |
| 250 | 5 μA | 4 μA |
| 500 | 9 μA | 8 μA |
| 800 | 14 μA | 13 μA |
| 1000 | 18 μA | 16 μA |

This result shows that linear calibration property within the range of 0-1000 mg/dl of glucose concentration can be provided. Each sensor was disposed every measurement of one sample. The fluctuation coefficient showing reproducibility (n=10) of each sensor at the glucose concentration of 100 mg/dl was 3.6% in the sensor A, and 3.5% in the sensor B.

(B) Embodiments of FIG. 6 to FIG. 9

Figure 6:
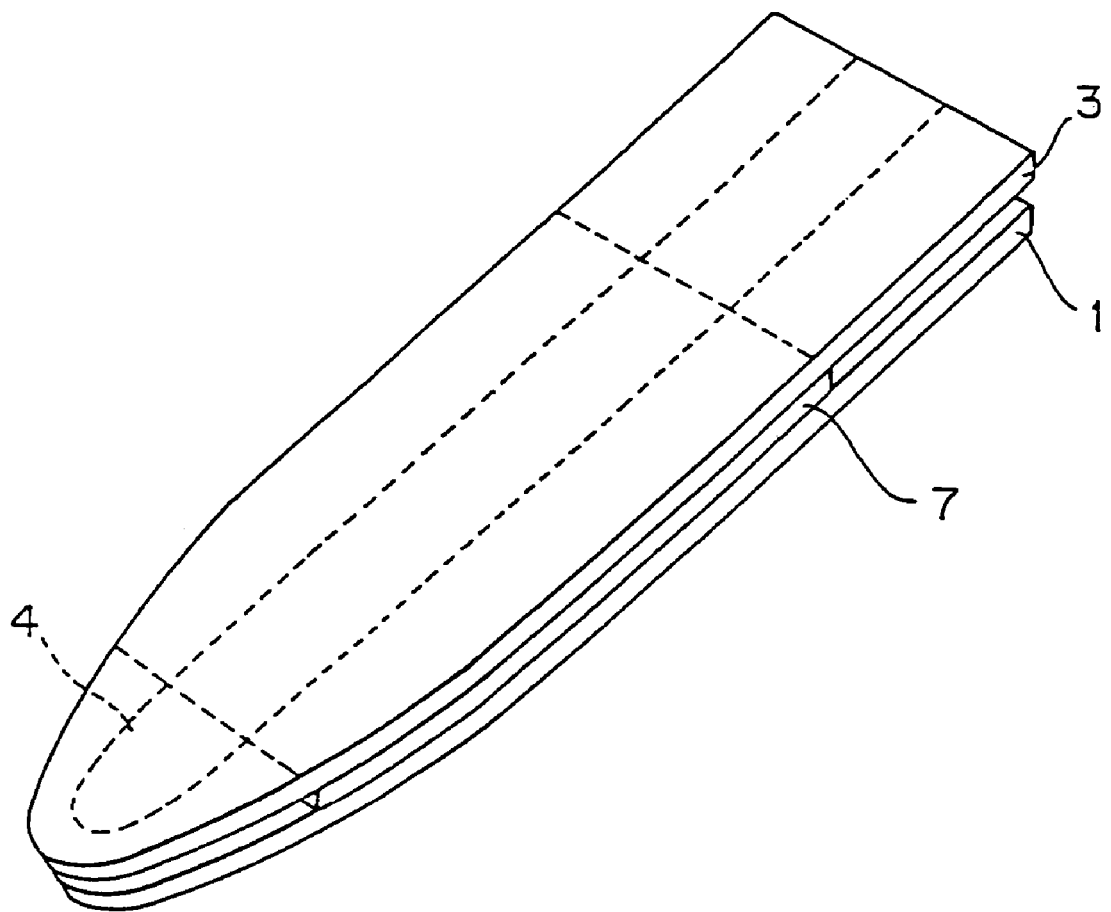
FIG. 6 is a perspective view of another embodiment of the biosensor according to this invention.
Figure 7:
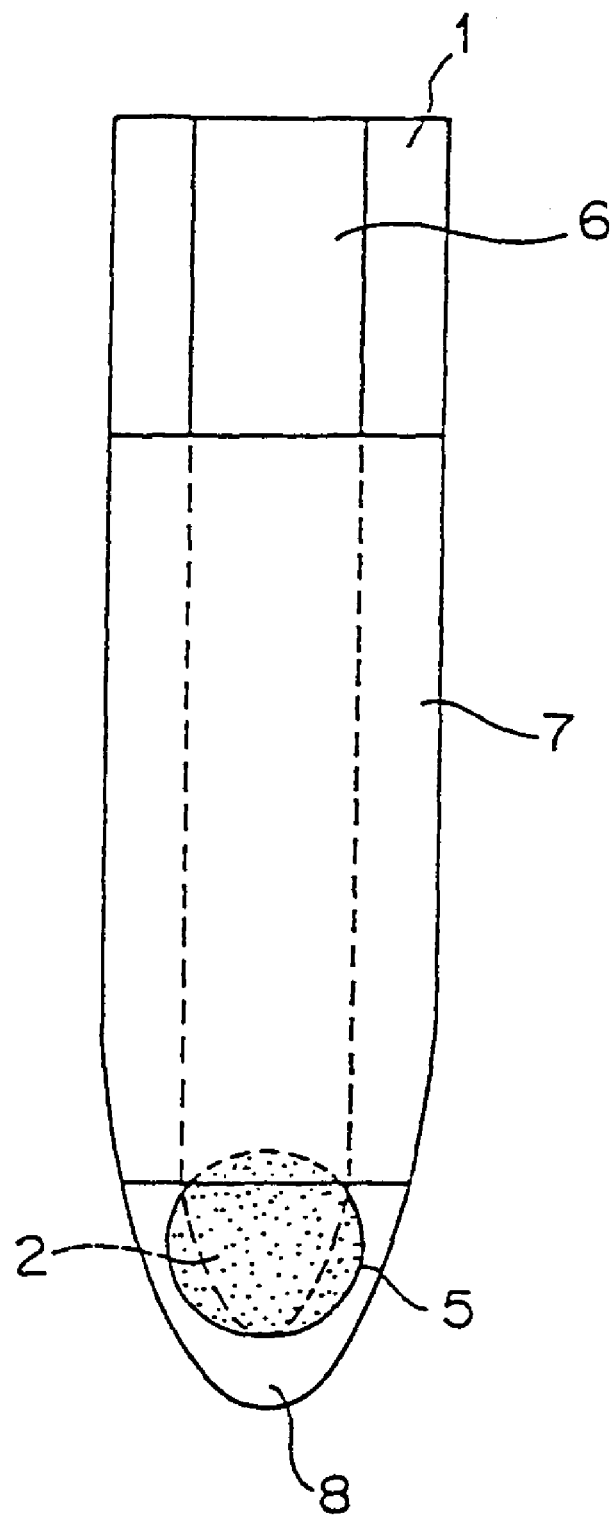
FIG. 7 is a plane view of a base having a working electrode provided thereon.
Figure 8:
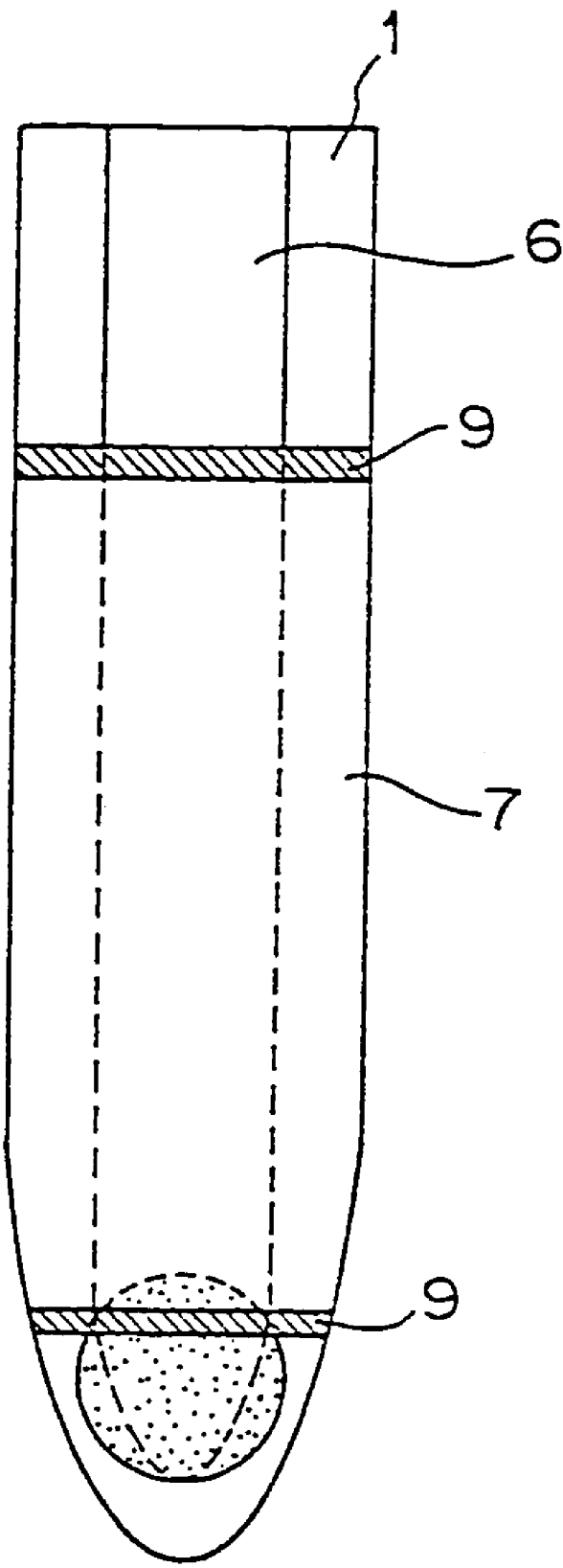
FIG. 8 is a plane view of a base having an insulating layer provided thereon.
Figure 9:
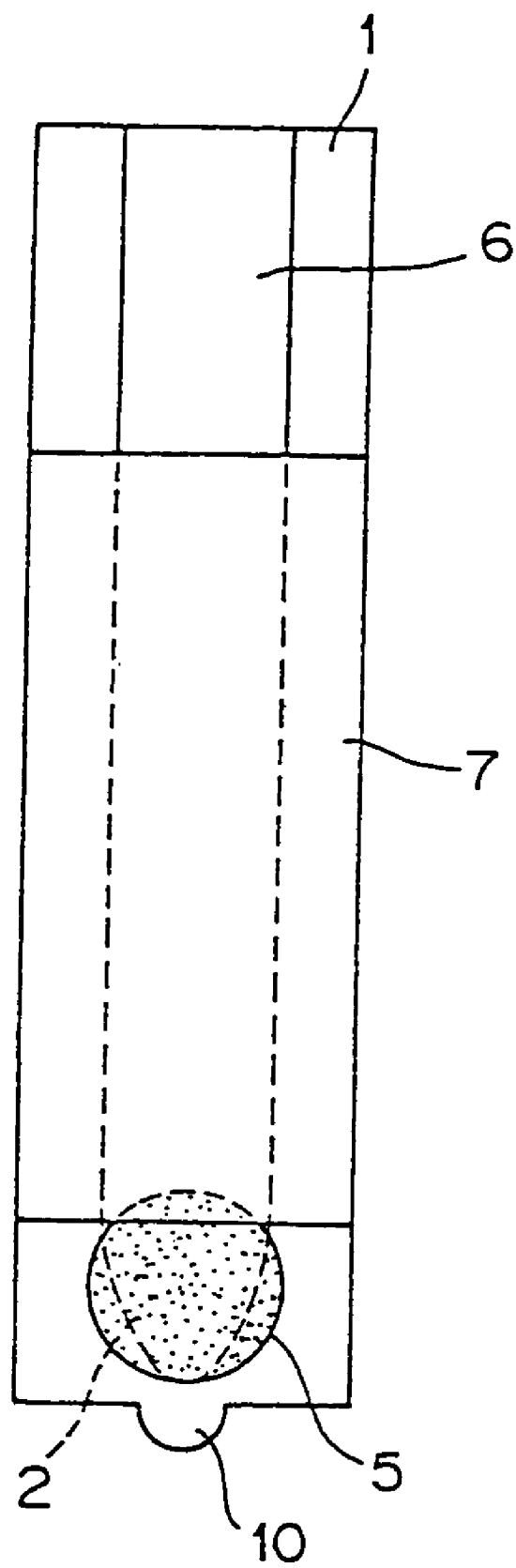
FIG. 9 is a plane view of a base having a protruded tip part.

FIG. 6 shows a perspective view of another embodiment of the biosensor according to this invention, and FIG. 7 shows a plane view of a base having a working electrode provided thereon. The part denoted at 11 in FIG. 6 is the space part for sucking and housing a sample.

The base 1 has the working electrode 2, the base 3 has its counter electrode 4, and an oxidoreductase-electron transmitter mixture layer 5 is formed on the working electrode 2 on the base tapered part 8 side. An adhesive layer 7 is formed in the part excluding the mixture layer and the lead part 6 of the working electrode 2.

The electrode is preferably used after polished with a nonwoven fabric.

Examples of the oxidoreductase to be immobilized include glucose oxidase, oxidase lactate, alcohol oxidase, pyruvate oxidase, glucose dehydrogenase, alcohol dehydrogenase, pyruvate dehydrogenase, antibody, and the like, and the concentration of an organic material such as glucose, lactic acid, alcohol, pyruvic acid, antigen or the like can be measured by them. The measurement of glucose concentration by glucose oxidase most generally used is illustrated below through an example of application dying method (adsorption method). In addition to the application drying method, conjugation bonding, ion bonding, cross linking and the like are employed as the immobilizing method of glucose oxidase.

The base having the working electrode provided thereon and the base having the counter electrode provided thereon are generally adhered together by use of a double-sided adhesive tape such as double-sided adhesive nonwoven fabric. The formed adhesive layer must have a thickness capable of keeping such a space that the working electrode does not make contact with the counter electrode, and it is set to about 100-500 μm (about 0.1-0.5 mm), preferably about 150-350 μm (about 0.15-0.35 mm).

Instead of the double-sided adhesive tape, an adhesive formed of acrylic resin can be applied to a prescribed position on one or both of the bases by screen printing to adhere both the bases together in the state keeping the above space. Further, an insulating film 9 formed of thermosetting polyester resin may be also provided under the adhesive layer 7 with a length larger than its length in a thickness of about 5-25 μm (Referred to FIG. 8).

On end side 8 of the base having the working electrode or counter electrode is tapered into a pointed form as shown in FIG. 6, so that the measuring sample can be directly collected even if it is a trace amount, and the contact with the electrode can be thus quickly performed. The one end side of the base having the electrode provided thereon may be made also into a protruding form 10 instead of the tapered form.

The biosensor according to this invention in which the working electrode having the oxidoreductase immobilized thereon and its counter electrode are arranged so as to have a facing structure by adhering the bases having these electrodes provided on the inside together through the adhesive layer is easy to manufacture, and the manufacturing cost can be also reduced.

EXAMPLE B1

Two polyethylene terephthalate bases tapered in one-side ends were prepared, carbon-made electrodes were formed on the respective bases in a thickness of 10 μm by screen printing. Onto one carbon-made electrode, 1.5 μl of a mixture (dopant) consisting of 10 mg of glucose oxidase (165800 unit) and 48 mg of potassium ferricyanide dissolved in 1 ml of water was dropped followed by drying under room temperature condition to form a glucose oxidase-potassium ferricyanide mixture layer (about 100 μm in thickness) as working electrode.

A base A having the thus-obtained mixture layer formed working electrode and a base B having its counter electrode were used, and they were stuck together with a double-sided adhesive tape (Product manufactured by Nitto Denko No. 500; 160 μm in thickness) as the adhesive layer in various embodiments as described below.

(1) The base A having the mixture layer formed working electrode and the base B having the counter electrode are stuck together by the adhesive layer provided on the base A side.

(2) The base A having the mixture layer formed working electrode and the base B are stuck together by the adhesive layer provided on the base A side.

(3) The bases A having the mixture layer formed working electrodes are mutually stuck by an adhesive layer (one forms the counter electrode).

(4) An insulating layer (formed by use of thermosetting polyester resin in a thickness of 20 μm by screen printing) is provided between each electrode and each base in (1) described above.

(5) Each electrode is polished with nonwoven fabric in (1) described above.

To the resulting glucose biosensors, 1 μl of a glucose aqueous solution (pH 5.0) having a concentration of 250 mg/dl was sucked, a voltage of 0.9V was applied between the working electrode and the counter electrode after it is allowed to stand for 20 seconds, and the current value after 10 seconds from the application was measured 10 times. A potentiogalvanostat (manufactured by Hokuto Denko HA501) and a function generator (manufactured by the same company HB-104) were used for the measurement. When CV value (ratio of standard deviation to average value) was calculated from the measured values, values of (1) 4.5%, (2) 4.3%, (3) 4.1%, (4) 4.4%, (5) 4.0% were obtained, respectively. The sensors were disposed every sample. When the measurement was performed with the glucose concentration being variously changed, the linearity was provided within the range of 0-1000 mg/dl.

EXAMPLE B2

In (1) of Example B1, the glucose aqueous solution was regulated to pH 7.0, and a dopant to which 10 mg of albumin was added was used. The CV value was 4.8%.

EXAMPLE B3

In (1) of Example B1, the glucose aqueous solution was regulated to pH 7.0, and the dopant was prepared by use of a 0.1M citric acid buffer solution (pH 5.0) instead of water. The CV value was 4.7%.

EXAMPLE B4

In (1) of Example B1, the glucose aqueous solution was regulated to pH 7.0, and the dopant was prepared by adding 10 mg of albumin and using a 0.1M citric acid buffer solution (pH 5.0) instead of water. The CV value was 4.6%.

EXAMPLE B5

In Example B4, a nonionic surface active agent (Product manufactured by UCC, Triton X-100) was added to the dopant in a concentration of 0.5 wt. %. The CV value was 4.5%.

EXAMPLE B6

In (1) of Example B1, a 0.5 wt. % aqueous solution of surface active agent (Triton X-100) was applied to the periphery of the working electrode followed by drying. The CV value was 4.4%.

With respect to the respective glucose biosensors of Example B2-B6, the linearity was obtained within the range of 0-1000 mg/dl of glucose concentration.

Figure 10:
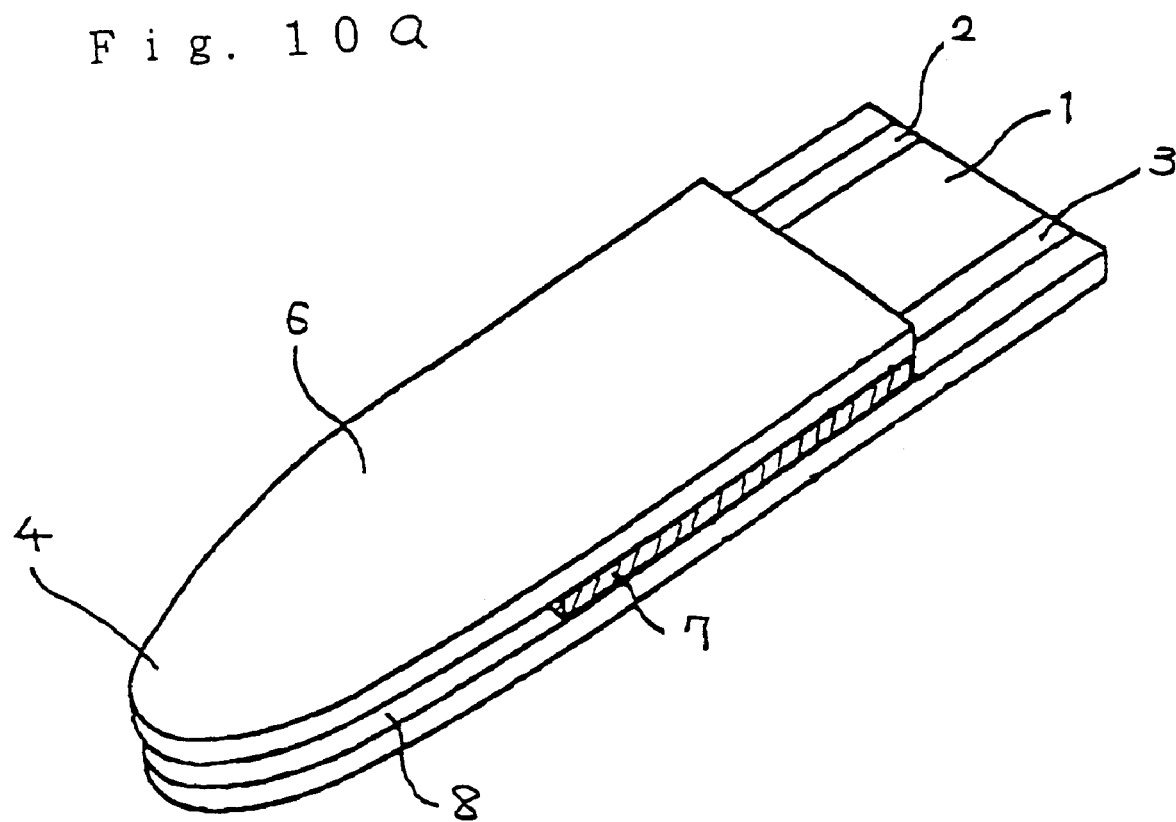
Figure 10B:
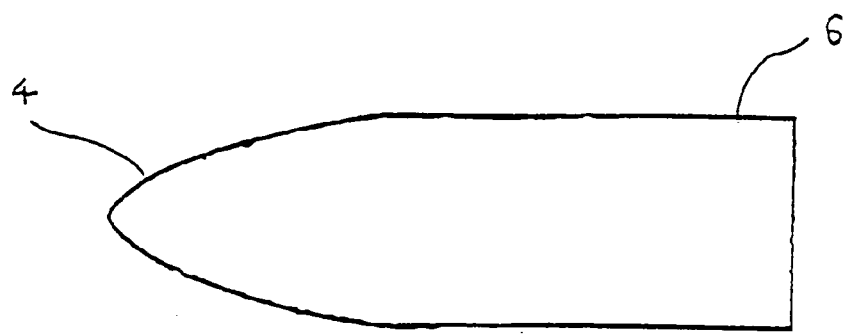
Figure 10B:
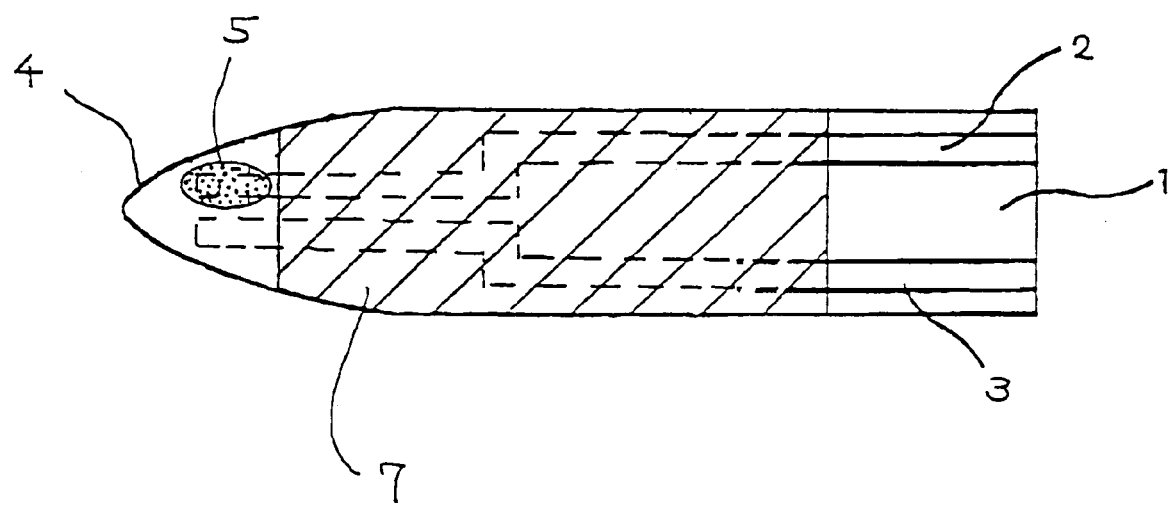

(C) Embodiments of FIG. 10a and FIG. 10b

FIG. 10a shows a perspective view of one embodiment of a biosensor according to this invention, and FIG. 10b shows a disassembled state view thereof.

The base 1 has both a working electrode 2 and the counter electrode 3, and an oxidoreductase-electron transmitter mixture layer 5 is formed on the working electrode 2 of the tapered part 4 of the base 1. Both the base 1 and the base (cover) 6 are adhered together by the adhesive layer 7. Denoted at 8 in FIG. 10a is the space part for sucking and housing the sample. The mixture layer 5 may be formed so as to cover both the working electrode 2 and the counter electrode 3.

EXAMPLE C

Two polyethylene terephthalate bases tapered on one-side ends were prepared, and two carbon-made electrodes were formed on one base in a thickness of 10 μm by screen printing. Onto the one carbon-made electrode, 1.5 μl of a mixture (dopant) consisting of 10 mg of glucose oxidase (165800 unit) and 48 mg of potassium ferricyanide dissolved in 1 ml of water was dropped followed by drying under room temperature condition to form a glucose oxidase-potassium ferricyanide mixture layer (about 100 μm in thickness) as working electrode. The other electrode formed on the same base was used as counter electrode.

The thus-obtained base A having the mixture layer formed working electrode and the counter electrode and the base B (cover) having no electrode were used, and they were stuck together with a double-sided adhesive tape (Product manufactured by Nitto Denko No. 500; 160 μm in thickness) as adhesive layer in various embodiments as described below.

(1) The base A and the base B were stuck together by the adhesive layer provided on the base A side.

(2) An insulating layer (formed 20 μm in thickness by use of thermosetting polyester resin by screen printing) was provided between the electrode and the base in the above (1).

To these glucose biosensors, 1 μl of a glucose aqueous solution having a concentration of 250 mg/dl (pH 5.0) was sucked, a voltage of 0.9V was applied between the working electrode and the counter electrode after it was allowed to stand for 20 seconds, and the current value after 10 seconds from the application was measured 10 times. A potentiogalvanostat (manufactured by Hokuto Denko HA 501) and a function generator (manufactured by the same company HB-104) were used for the measurement. When the CV value (ratio of standard deviation to average value) was calculated from the measured values, values of (1) 4.3%, (2) 4.0% were obtained, respectively. The sensors were disposed every sample. When the measurement was performed with the glucose concentration being variously changed, the linearity was obtained within the range of 0-1000 mg/dl.

(D) Embodiments of FIGS. 11-14

In a biosensor of the embodiment in which one end side of each base is tapered, and the tip parts of the working electrode and the counter electrode are provided on each tapered part, the separated electrodes are provided on the base tapered parts having a pointed shape. Therefore, it is extremely convenient since a measuring solution such as glucose aqueous solution can be directly collected even when it is a trace amount, and the contact with the working electrode can be thus quickly performed. It also has an operational advantage that the affected part is hardly damaged in blood sampling on finger.

Figure 11:
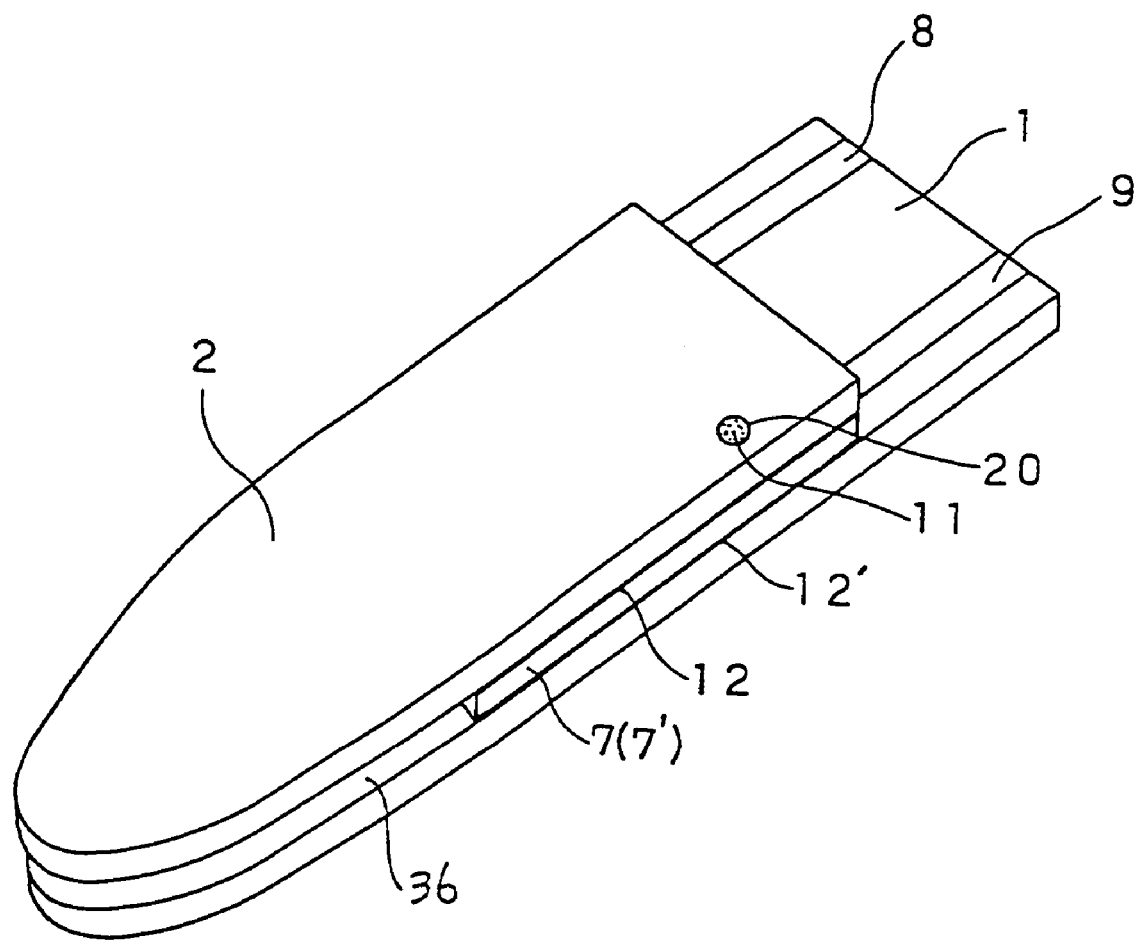
FIG. 11 is a perspective view of another embodiment of the biosensor according to this invention.
Figure 12:
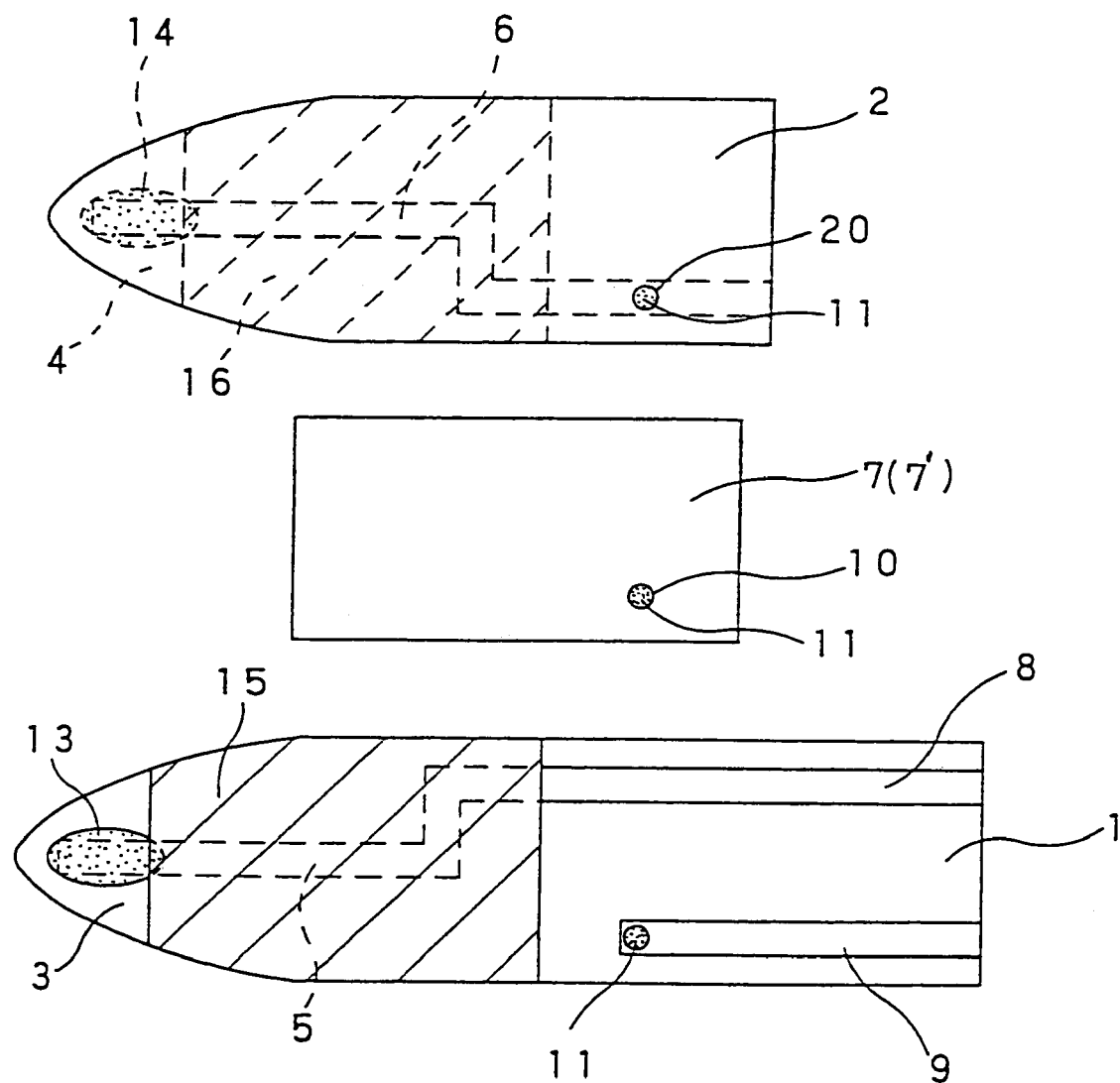
FIG. 12 is a disassembled state view of each component in the embodiment of FIG. 11.

A biosensor having a tapered part is shown in FIG. 11 (perspective view) and FIG. 12 (disassembled state view of each component). The space for sucking and housing the sample is denoted at 36 in FIG. 11.

Two bases, or a longer lower base 1 and a shorter upper base 2 are prepared, and tapered parts 3, 4 are formed on one-end sides of the respective bases. A working electrode 5 and a counter electrode 6 are provided on the inside of the bases 1, 2, respectively, so that the tip parts are situated on the tapered parts 3, 4, and these electrodes have a facing structure since the respective bases are adhered through an adhesive layer 7 or a spacer 7'.

The lead parts 8, 9 for the electrodes 5, 6 are formed on the lower base 1. At that time, each lead part 8, 9 is formed so that the end part is situated in a position never superposed on the upper base 2 in order to lay the end part of each lead part into open state allowing the connection with a connector requiring no special structure. These electrodes and their lead parts are preferably polished with a cloth.

An oxidoreductase is immobilized on the working electrode situated on the tapered part tip, and the oxidoreductase is preferably formed as a mixture layer 13 with an electron transmitter (mediator). It is preferred to provide an oxidoreductase-electron transmitter mixture layer 14 also on the counter electrode situated on the tapered part tip. Plastic insulating films 15, 16 such as thermosetting polyester are provided about 0.1-0.3 mm in thickness on the working electrode and the counter electrode on which the mixture layers can not be provided.

To conduct the electrode 6 on the upper base 2 to the lead part 9 formed on the lower base 1, the adhesive layer 7 or the spacer 7' has a bored part (through-hole) 10, and a conductive material 11 is filled therein by silver paste, carbon paste or soldering.

The adhesion of the base having the working electrode and the base having the counter electrode by the adhesive layer is generally performed by a double-sided adhesive tape such as double-sided adhesive nonwoven fabric. The formed adhesive layer must have a thickness capable of keeping such a space that the working electrode does not make contact with the counter electrode, and it is set to about 100-500 μm (about 0.1-0.5 mm), preferably about 150-350 μm (about 0.15-0.35 mm).

Instead of the double-sided adhesive tape, an adhesive formed of acrylic resin can be applied to a prescribed position on one or both of the bases by screen printing to adhere both the bases together in the state keeping the above space. Further, an insulating film 16 formed of thermosetting polyester resin can be provided under the adhesive layer 7 with a length larger than its length in a thickness of about 5-25 μm.

The adhesion of the base having the working electrode and the base having the counter electrode by the spacer is performed by adhesives 12, 12' on both sides of the spacer.

In the adhesion of each base by the adhesive layer or spacer, it is operationally easy to provide a hole 20 on the upper base 2 to fill the conductive material 11 through it. In the adhesion by the adhesive layer, the size of the hole 10 provided on the double adhesive tape 7, for example, is desirably larger than the area of the hole 20 provided on the upper base 2. In this case, the conductive material 11 such as silver paste turns around and makes contact with the exposed part of the lead part 9 of the lower base 1 to ensure a sufficient continuity there.

When a reference electrode is provided the reference electrode is formed by forming a silver electrode on a reference electrode lead by screen printing, vapor deposition, or sputtering followed by constant current electrolysis or dipping in ferrous chloride aqueous solution, by applying and laminating silver chloride by screen printing, or the like. The reference electrode can be set on either of the working electrode-side base and the counter electrode-side base, but it is preferably set on the working electrode-side base. Actually, the electrode is formed on the same base so as to draw the lead part to the surface side through the through-hole in parallel to the other electrode. The reference electrode part must not be covered with the mixture layer.

Figure 13:
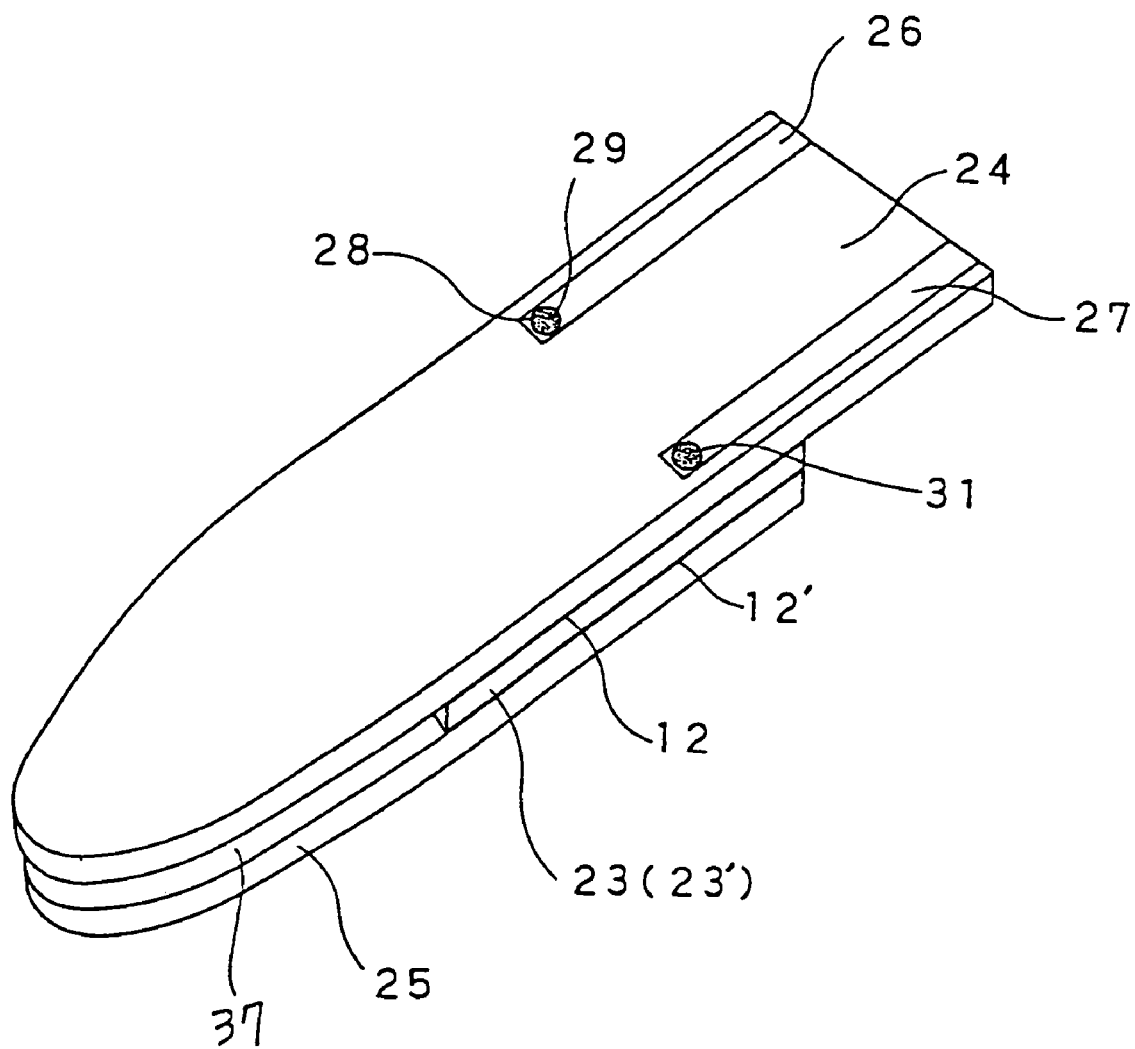
FIG. 13 is a perspective view of the other embodiment of the biosensor according to this invention.
Figure 14:
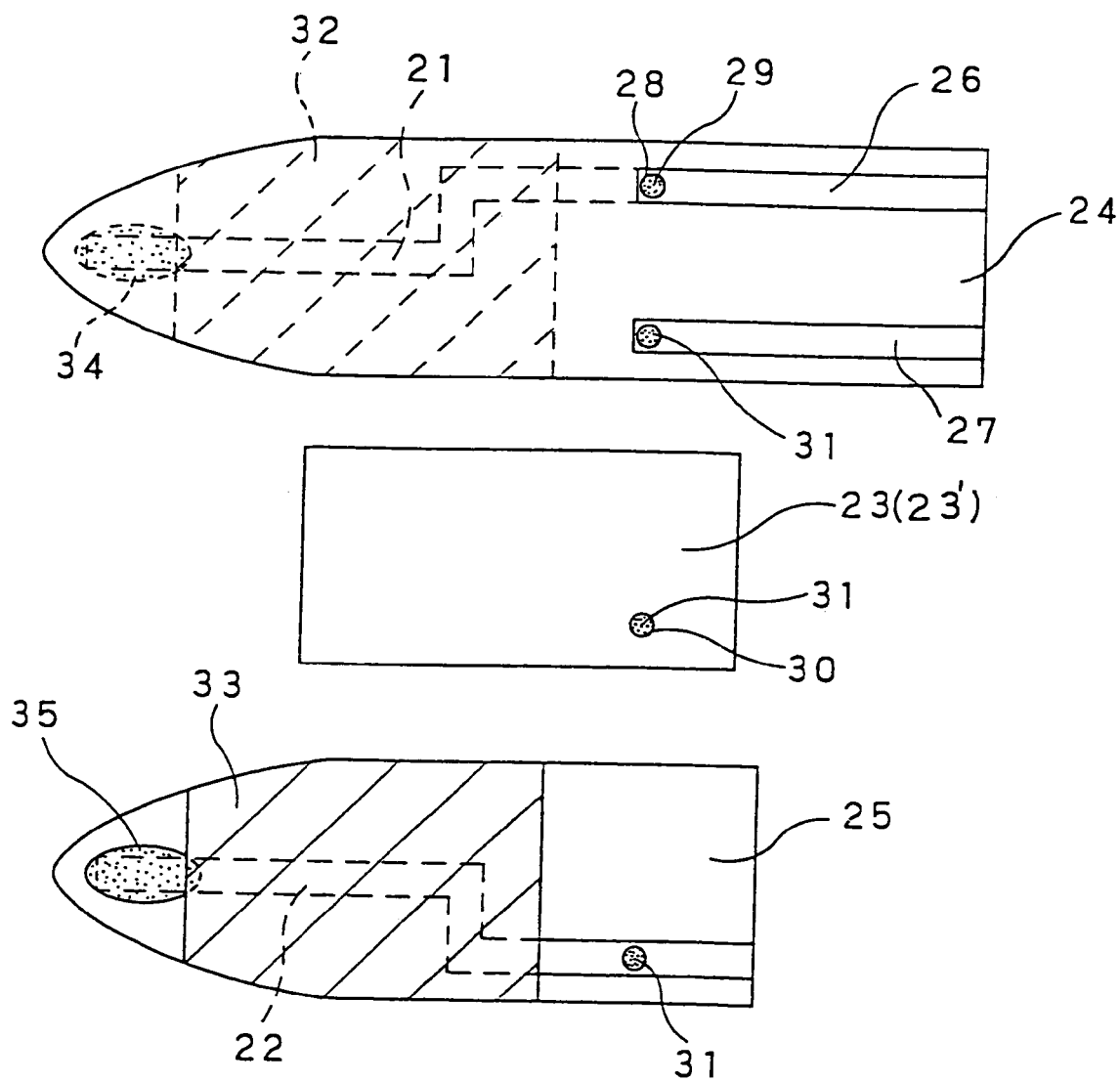
FIG. 14 is a disassembled state view of each component in the embodiment of FIG. 13.

FIG. 14 shows a disassembled state view of each component in another embodiment having a tapered part. The part denoted at 37 in FIG. 13 is the space part for sucking and housing a sample.

A working electrode 21 and a counter electrode 22 are formed on the inside of a longer upper base 24 and a shorter lower base 25 through an adhesive layer 23 or a spacer 23' so as to have a facing structure, respectively, and the lead parts 26, 27 of the electrodes are formed on the surface side of the upper base 24, respectively, in the same manner as in the embodiment of FIGS. 11-12. The formation of mixture layers 34, 35 onto the working electrode 21 and the counter electrode 22 is also performed in the same manner as the embodiment of FIGS. 11-12.

In the embodiment of FIG. 14, the upper base 24 has a bored part (through-hole) 28 so as to conduct the electrode 21 provided on the inside (reverse side) of the upper base 24 to the lead part 26 provided on the surface side, a conductive material 29 is filled therein, and a conductive material 31 is filled in the through-hole 30 of the adhesive layer 23 or the spacer 23' in order to conduct the electrode 22 provided on the lower base 25 to the lead part 27 provided on the upper electrode 24. Denoted at 32, 33 are insulating films.

As the base, insulating bases such as plastic represented by polyethylene terephthalate, biodegradable plastics, glass, ceramics, paper are used in film, sheet or plate form. The formation of the working electrode, the counter electrode, and their lead parts is performed by means of screen printing using paste of carbon, silver, or gold or foil application using palladium foil onto both sides bordered with the bored part.

Although the biosensor having the facing structure by interposing the adhesive layer or spacer between the base having the working electrode arranged thereon and the base having the counter electrode arranged thereon required a connector having a special structure since the electrode lead parts are mutually opposed in the inner part, the lead parts of the working electrode and the counter electrode are made into opened end parts, whereby a biosensor requiring no special connector can be provided.

Such a biosensor is easy to manufacture and measure by setting the working electrode and the counter electrode so as to have a facing structure, and can be effectively used, as a disposable biosensor using a liquid concentrate sample as measuring solution, for domestic medical examination (self-care), particularly, self-management of diabetes and prevention and early detection of diabetes by measurement of blood sugar or urine sugar, and a wide use such as use for glucose management in food manufacturing process can be expected.

EXAMPLE D1

The biosensor of the embodiment shown in FIGS. 11-12 was manufactured as follows.

Two long and short polyethylene terephthalate films (0.25 mm in thickness) were prepared as a lower base and an upper base, respectively, and a working electrode, its lead part, and a counter electrode lead part were formed on the lower base, and a counter electrode and a part of its lead part on the upper base in a width of 1.0 mm and a thickness of 10 µm by screen printing using carbon paste, respectively. Further, prescribed insulating films were provided on the working electrode and the counter electrode by screen printing using thermosetting polyester.

On the working electrode of the longer polyethylene terephthalate film having the thus-formed working electrode, 1.5 µl of a mixture (dope solution) consisting of 10 mg of glucose oxidase (165800 unit/g) and 48 mg of potassium ferricyanide dissolved in 1 ml of water was dropped followed by drying under room temperature condition to form a mixture layer. The mixture layer was also formed on the counter electrode in the same manner. Prior to the formation of the mixture layers, the working electrode part and the counter electrode part were polished with nonwoven fabric.

The mixture layer formed electrode bases were mutually stuck by use of a spacer with adhesive on both sides (material: polyethylene terephthalate, thickness: 0.25 mm) to manufacture a glucose biosensor having electrodes of the facing structure. Silver was filled in the through-hole (diameter: 0.8 mm) of the spacer by applying silver paste to ensure the continuity between the counter electrode and its lead part.

To the above glucose-biosensor, 1 µl of a glucose aqueous solution sample (concentration: 250 mg/ml) of pH 5.0 was sucked, a voltage of 0.9V was applied between the working electrode and the counter electrode after it was allowed to stand for 80 seconds, and the current value (unit: µA) after 10 seconds from the application was measured. The measurement was performed five times, and the average value and the CV value (ratio of standard deviation to average value) were calculated. A potentiogalvanostat (manufactured by Hokuto Denko HA501) and a function generator (manufactured by the same company HB-104) were used for the measurement, and the above glucose biosensor was mounted on this device to perform the measurement. The sensor was disposed every sample measurement.

| 24.0 | 22.5 | 24.5 | 23.0 | 26.0 |
|---|---|---|---|---|
| | Average value: 24.0 | | | CV value: 5.7% |

EXAMPLE D2

The biosensor of the embodiment shown in FIGS. 13-14 was manufactured as follows.

Two long and short polyethylene terephthalate films were prepared as an upper base and a lower base, and a working electrode, its lead part, and a counter electrode lead part were formed on the upper base, and a counter electrode and a part of the lead part on the lower base in a width 1.0 mm and a thickness 10 μm by screen printing using carbon paste, respectively. A prescribed insulating film was provided in the same manner as in Example D1. The formation of the mixture layers onto the working electrode and the counter electrode was also performed in the same manner as in Example D1.

These mixture layer-formed electrode bases were mutually stuck with a spacer with adhesive on both sides to manufacture a glucose biosensor having electrodes of the facing structure. Silver paste was applied to each through-hole of the upper base and the spacer to fill silver, whereby the continuity of the working electrode and its lead part to the counter electrode and its lead part was ensured.

The measurement by use of the thus-manufactured glucose biosensor was performed in the same manner as in Example D1 to provide the following result.

| 24.0 | 22.0 | 24.5 | 24.5 | 26.0 |
|---|---|---|---|---|
| Average value: 24.2 | | | CV value: 6.0% | |

EXAMPLE D3

A double-sided adhesive tape (Product manufactured by Nitto Denko No. 500, thickness: 0.16 mm) was used instead of the spacer with adhesive on both sides in Example D1. The size of the hole bored in the double-sided adhesive tape was set larger than the size of the hole provided on the upper base.

The measurement by use of the thus-manufactured glucose biosensor was performed in the same manner as in Example D1, and the following result was obtained.

| 24.0 | 24.5 | 22.5 | 23.0 | 24.0 |
|---|---|---|---|---|
| Average value: 23.7 | | | CV value: 3.8% | |

EXAMPLE D4

The mixture layer was formed only on the working electrode in Example D3, and the following result was obtained.

| 25.9 | 24.0 | 23.0 | 24.5 | 23.0 |
|---|---|---|---|---|
| Average value: 24.1 | | | CV value: 5.0% | |

In each of Examples D1-D4 described above, linearity was provided within the calibration range of 0-1000 mg/dl of glucose aqueous solution concentration.

Figure 15:
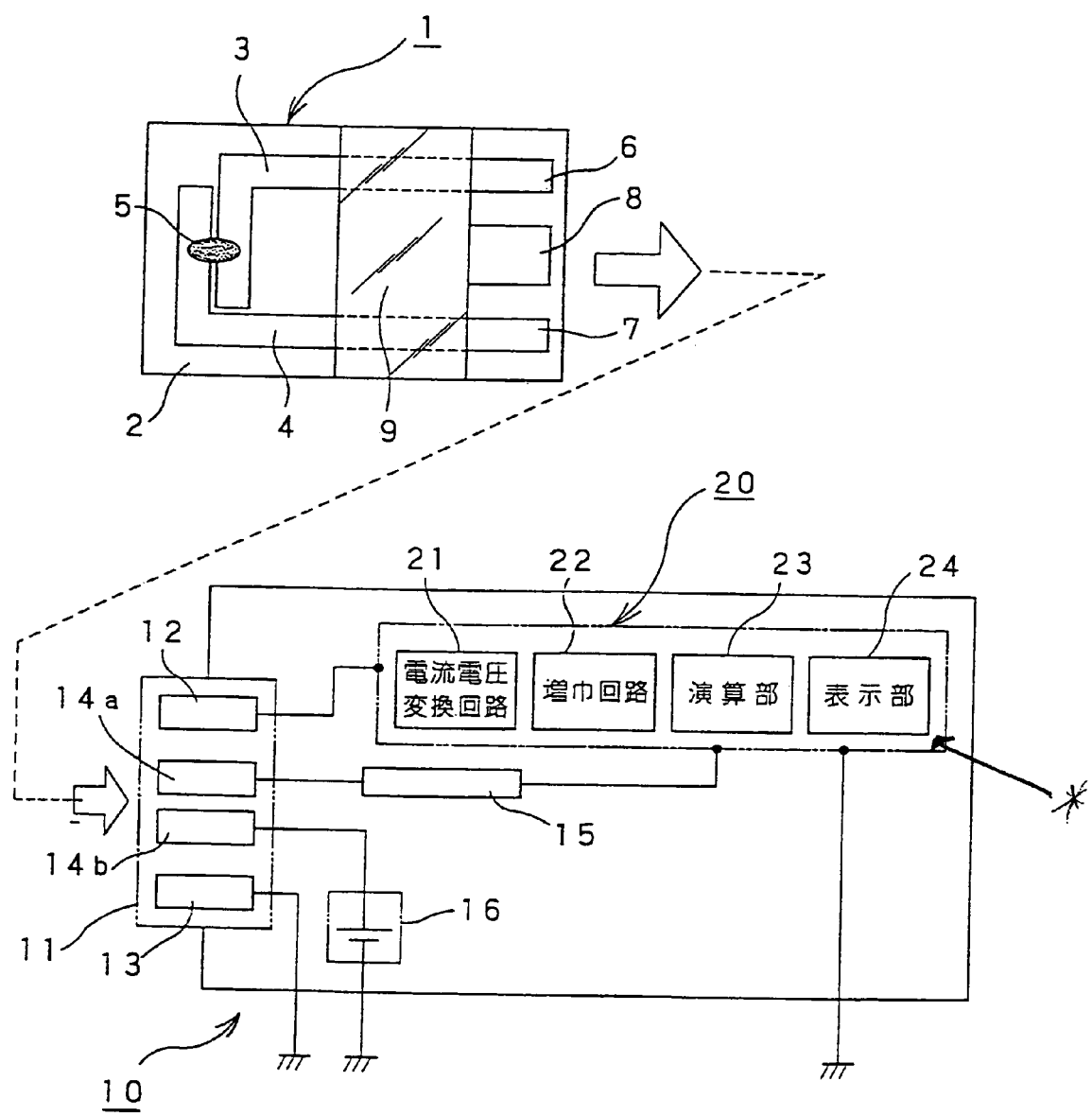
FIG. 15 is a system constitution view showing the biosensor device of the other embodiment according to this invention.

(E) Embodiments of FIG. 15

Bioelectronic studies for applying biodynamics to electronic field have been advanced. A biosensor in this bioelectronic field is a device utilizing the excellent molecule identifying function possessed by organism, which is regarded as a promising device capable of quickly and easily measuring a chemical material. Such a biosensor is applied as a trace sample measuring sensor, and has a wide applicable field such as disposable use for domestic medical examination (self-care) of measuring blood sugar or urine sugar to self-manage and prevent diabetes, and industrial use for sampling quality inspection of product on production line.

As a concrete example of measurement, a material to be measured in a collected aqueous solution sample is dropped to a reaction part, and the reduced material generated by, for example, enzyme reaction is oxidized, whereby the element current value by the oxidation is taken out and detected. The measured value equivalent to the element current value is determined in reference to a data table, and it is outputted and displayed.

In such a biosensor, an optical system is used as a judging means for recognizing whether the sensor is inserted into the device body and laid in measurable state or not to detect the reflected light or transmitted light changed by the insertion of the sensor.

The biosensor device according to this invention is enhanced in reliability of the device, improved in a series of operability up to measurement end by avoiding the operation by the wrong recognition in insertion of a foreign matter other than the sensor, and also advantageous in cost.

In the biosensor device of this invention, an element reaction sensor member inserted to the connector part of a device body in such a manner as to be attachable and detachable has each output terminal of a working electrode and a counter electrode to be electrically connected to a corresponding input terminal on connector part side by insertion, and an element reaction part is formed on at least the working electrode of the working electrode and the counter electrode. The element reaction sensor member further has a sensor insertion judging electrode, and the connector part of the device body has two input terminals with which the sensor insertion judging electrode output terminal makes contact, so that the system of the device body is started by the contact with the two input terminals to judge the insertion of the sensor by a control part.

In this case, the control part judges the dropping of a material to be measured by a signal for laying the working electrode and the counter electrode into close circuit by the dropping of the material to the element reaction part, starts to count the residual time up to a preset measurement end, and transmits the count signal to a display part provided on the device body to display it.

FIG. 15 shows a system constitution view of a biosensor device according to the other embodiment of this invention. The system mainly has a sensor 1 for taking the current value generated by an element reaction by dropping an aqueous solution sample to be measured, and a device body 10 for converting and displaying the taken current value to an equivalent measured value. The sensor 1 is disposable, and easily attachable and detachable to a connector part 11 provided on the device body 10 side.

For a rectangular insulating base 2 for forming the body of the sensor 1, ceramics, glass, paper, biodegradable material (for example, microorganism producing polyester) and plastic material such as polyethylene terephthalate are used. A pair of electrodes 3, 4 for taking the element current generated by enzyme reaction of, for example, an oxidoreductase are pattern-formed on the base 2. Both the electrodes 3, 4 can be defined as the names of the working electrode 3 and the counter electrode 4. As the electrode material, conductive metals such as carbon, silver, gold, palladium are used, and they are pattern-formed by screen printing, sticking, vapor deposition, or sputtering.

A mixture layer 5 which is the element reaction part is formed on the working electrode 3 or on both the working electrode 3 and the counter electrode 4. The mixture layer 5 can be formed by use of a mixture of an oxidoreductase and an electron transmitter (mediator), for example, a mixture of glucose oxidase and potassium ferricyanide. In most of disposable glucose biosensors using glucose oxidase which is a typical oxidoreductase, the liquid concentrate sample of a material to be measured is collected for measurement. The method of indirectly determining the glucose aqueous solution concentration by the element current value by oxidation is known, and it comprises generating gluconolactone simultaneously with reducing ferricyan ion to form ferrocyan ion by glucose oxidase effect, and oxidizing the ferrocyan ion on the working electrode 3 to detect and measure the element current value.

The respective end parts (lead parts) of the working electrode 3 and the counter electrode 4 on the opposite side to the position having the mixture layer 5 are formed as a pair of opposed output terminals 6, 7. A sensor insertion judging electrode (hereinafter referred to as sensor insertion signal terminal) 8 which is the essential member of this invention is formed on the base 2 between the output terminals 6, 7. This sensor insertion signal terminal 8 is generally formed of the same material as the working electrode 3 and the counter electrode 4 in the same forming method. An insulating layer 9 is formed on a part of the base 2 by screen printing by use of thermosetting polyester material so as to lay the terminals 6, 7, 8 into the mutually electrically insulated state.

On the other hand, the device body 10 is formed of the following parts. It has a connector part 11 for the part for inserting and electrically connecting the disposable sensor 1 in measurement. The connector part 11 is formed of four connector pins in total of an input terminal 12 to be connected to the output terminal 6 of the working electrode 3 on the sensor 1 side, an input terminal 13 connected to the output terminal 7 of the counter electrode 4, and two input terminals 14a, 14b corresponding to the sensor insertion signal terminal 8. Of the two input terminals 14a, 14b provided in conformation to the sensor insertion signal terminal 8, one input terminal 14a is connected to a regulator part 15, and the other input terminal 14b to a power source circuit 16. Thus, the two input terminals 14a, 14b are connected in short-circuit state by the contact with the signal terminal 8 by the insertion of the sensor from the open circuit state to form a closed circuit, and the regulator part 15 is connected to the power source circuit 16, whereby a power is supplied to a control part 20 to be described later to start the system. Namely, the sensor insertion signal terminal 8 is provided as the essential member in order to detect and judge the insertion of the sensor 1 to the device body 10 and start up the system.

As the part for controlling the system, the device body 10 has a control part 20 formed of a CPU (central processing unit) by microcomputer. The control part 20 is formed of a current-voltage converting circuit 21 for converting the detected current to voltage value, an amplifying circuit 22 for amplifying the converted voltage signal, an arithmetic part 23 for arithmetically processing on the basis of the input data signal, and a display part 24 such as LCD (liquid crystal display device) for digitally displaying the value processed in the arithmetic part 23 as measurement data. In the CPU, the entire control is performed on the basis of signals inputted and outputted through an I/O port from each part and each circuit.

The operation and action of the biosensor device described above are illustrated. In measurement, the sensor 1 is inserted to the connector part 11 of the device body 10. In this sensor inserting stage, an aqueous solution sample containing a collected material to be measured is not dropped to the mixture layer 5 of the element reaction part on the sensor 1 side. Thus, the working electrode 3 and the counter electrode 4 of the sensor 1 are still in open state.

Both the output terminals 6, 7 of the working electrode 3 and the counter electrode 4 of the sensor 1 are connected to the corresponding input terminals 12, 13 on the device body 10 side by the insertion of the sensor. The sensor insertion signal terminal 8 is also connected to the two input terminals 14a, 14b in the connector part 11 of the device body 10. Then, they are laid into short-circuit state to form a closed circuit, the regulator part 15 is connected to the power source circuit 16 to supply a power to the control part 20. The control part 20 judges the insertion of the sensor 1 by the starting of the system. A voltage is applied between the working electrode 3 and the counter electrode 4 by a control signal outputted from the control part 20 according to this judgment of sensor insertion.

When a 0.5 wt. % of glucose aqueous solution sample, for example, is dropped onto the mixture layer 5 of the sensor 1, the working electrode 3 and the counter electrode 4 are laid in short-circuit state to form a closed circuit. According to this close signal, the control part 20 judges the dropping of the glucose aqueous solution sample, and interrupts the voltage supply applied between the working electrode 3 and the counter electrode 4. Synchronously to this, the control part 20 starts to count the residual time to the measurement end with a preset time numerical as starting point, for example, 30 seconds. The counted residual time is displayed on the display part 24 so as to be recognizable by an operator. When the residual time reaches a set time, the voltage of a preset value for reaction is applied between the working electrode 3 and the counter electrode 4. By this voltage reapplication, the reduced material generated by the enzyme reaction of the glucose aqueous solution sample dropped onto the mixture layer 5 is oxidized on the working electrode 3, and the element current value generated by the oxidation is detected and read.

After the reacting voltage is applied only for a fixed time, the detected and read element current value is converted into voltage value in the current-voltage converting circuit 21, and the converted voltage value is amplified by the amplifying circuit 22. The calculation result data in the arithmetic part 23 in reference to the data table corresponding to the amplified voltage is displayed on the display part 24.

When the sensor 1 is not removed from the device body 10 after the measurement result data is displayed for a fixed time, the power source circuit 16 is OFF. Even when the sensor 1 is laid into leaving state, the power source circuit 16 on the device body 10 side can be automatically OFF after the lapse of, for example, 2 minutes. The power source circuit 16 can be switched OFF also by removing the sensor 1.

The sensor 1 having the working electrode 3 and the counter electrode 4 flat pattern-formed within the same plane on the rectangular body base 2 was described above as an example, but this invention is not limited by this electrode pattern. For example, the working electrode 3 and the counter electrode 4 are formed on the inside of the opposed bases, whereby a facing structure can be formed. The arranging position of the sensor insertion signal terminal 8 is also optionally selected. Further, the display form and display character style for display of measurable state, count display of measuring time, concentration display of an intended material in a collected sample, and the like can be also optionally set.

According to the biosensor device of this invention, since the insertion of the sensor to the device body can be surely detected by providing the insertion signal terminal formed of the sensor insertion judging electrode on the-sensor side, there is no fear of causing a trouble such as operation by the wrong recognition in insertion of a foreign matter other than the sensor as in the past. Since the sensor insertion is detected by an electric signal without using a conventional complicated and expensive optical system as the means for detecting and judging the sensor insertion, this device is suitable for an inexpensive and easy disposable device.

EXAMPLE E1

When an element reaction sensor member having a working electrode and a counter electrode by screen printing using carbon paste, a sensor insertion judging electrode by screen printing using silver paste, and a thermosetting polyester insulating layer by screen printing formed on a polyethylene terephthalate base, respectively, was inserted to the connector part of a system body, a power source was automatically ON, and "READY" was displayed on a display part.

When a 500 mg/dl glucose aqueous solution was dropped onto a sensor mixture layer (mixture layer of glucose oxidase and potassium ferricyanide), "residual time 30 seconds" was displayed on the body display part, and the countdown of the residual time was started. When "residual time 10 seconds" was displayed, a voltage of 1.0V was applied between both the electrodes, the reduced material generated by the enzyme reaction was oxidized by the working electrode surface after 10 seconds from it, the oxidizing current value generated then was read into the body circuit part within the system, and converted into voltage followed by amplification, and the value according to it was determined in reference to a data table. As a display value, "500 mg/dl" was outputted to the display part. When the sensor was left as in the inserted state, the power source of the body was automatically OFF after 2 minutes.

What is claimed is:

1. A biosensor comprising:
a proximal end and a distal end;
a first layer having a first length and a second layer having a second length, the first and second layers being fixed together by a third layer having a third length;
a tapered part located at the proximal end;
a working electrode provided on a first layer and a counter electrode provided on a second layer, wherein the tip part of the working electrode is provided on the tapered part; and
wherein leads for the working and the counter electrodes extend from the tapered part to the distal end.

2. The biosensor of claim 1, wherein the tapered part includes an opening for admitting sample.

3. The biosensor of claim 2, further comprising a space for housing a sample and the opening is in communication with the space for housing the sample.

4. The biosensor of claim 3, wherein the space has a volume that ranges from about 0.5-10 microliters.

5. The biosensor of claim 1, wherein a tip part of the counter electrode is provided on the tapered part.

6. The biosensor of claim 1, further comprising a reference electrode and a tip part of the reference electrode is provided on the tapered part.

7. The biosensor of claim 6, wherein the working electrode and reference electrode are provided on the same layer.

8. The biosensor of claim 7, wherein the same layer is the first layer and a length of the first layer is greater than a length of the second layer.

9. The biosensor of claim 6, wherein the counter electrode and reference electrode are provided on the same layer.

10. The biosensor of claim 1, wherein the third layer comprises adhesive.

11. The biosensor of claim 1, further comprising an analyte-responsive enzyme.

12. The biosensor of claim 11, wherein the analyte-responsive enzyme is selected from the group of glucose oxidase and glucose dehydrogenase.

13. The biosensor of claim 1, wherein the biosensor is connectable to a device body having a control part including a display part, and the bio sensor further comprises a biosensor insertion signal terminal for interconnecting, upon connecting the biosensor to the device body, two input terminals of the device body to start the control part of the device body.

14. A biosensor comprising:
a proximal end and a distal end,
a first plate having a first length,
a second plate having a second length,
a space formed between the two plates for housing a sample therein,
a layer having a third length for fixing the two plates together,
the space for housing the sample being partially opened at a peripheral part thereof and partially closed by the layer,
a working electrode provided on the first plate and a counter electrode provided on the second plate and fixed relative to the working electrode,
a tapered part located at the proximal end, and
a tip part of the working and counter electrodes being provided on the tapered part,
wherein leads for the working and counter electrodes extend from the tapered part to the distal end.

15. The biosensor of claim 14, further comprising an analyte-responsive enzyme.

16. The biosensor of claim 15, wherein the analyte-responsive enzyme is selected from the group of glucose oxidase and glucose dehydrogenase.

17. The biosensor of claim 14, wherein the biosensor is connectable to a device body having a control part including a display part and the biosensor further comprises a biosensor insertion signal terminal for interconnecting, upon connecting the biosensor to the device body, two input terminals of the device body to start the control part of the device body.

18. The biosensor of claim 14, wherein the tapered part includes an opening for admitting sample.

19. The biosensor of claim 18, further comprising a space for housing a sample and the opening is in communication with the space for housing a sample.

20. The biosensor of claim 19, wherein the space has a volume that ranges from about 0.5-10 microliters.

21. The biosensor of claim 14, wherein the biosensor further comprises a reference electrode and a tip part of the reference electrode is provided on the tapered part.

22. The biosensor of claim 21, wherein the working electrode and reference electrode are provided on the same layer.

23. The biosensor of claim 21, wherein the counter electrode and reference electrode are provided on the same layer.

24. A method of measuring a concentration of an analyte in a subject, the method comprising:
contacting body fluid of the subject with a biosensor to generate an electrical signal, the biosensor having a proximal end and a distal end, at least three layers, a working electrode provided on a first layer and a counter electrode provided on a second layer, a tapered part located at the proximal end, and a tip part of the working electrode provided on the tapered part, wherein the three different layers have different lengths and leads for the working and counter electrodes extend from the tapered part to the distal end, and determining from the generated electrical signal a concentration of an analyte in body fluid.

25. The method of measuring a concentration of an analyte in the subject as claimed in claim 24, wherein the body fluid is contacted with the biosensor at the tapered part.

26. The method of measuring a concentration of an analyte in the subject as claimed in claim 25, wherein the tapered part comprises an opening in communication with a space for housing the body fluid, and the method comprises admitting the body fluid into the space through the opening in the tapered part.

27. The method of measuring a concentration of an analyte in the subject as claimed in claim 24, wherein the body fluid ranges from about 0.5 to about 10 microliters.

28. The method of measuring a concentration of an analyte in the subject as claimed in claim 24, wherein the biosensor comprises an analyte-responsive enzyme.

29. The method of measuring a concentration of an analyte in the subject as claimed in claim 28, wherein the analyte-responsive enzyme is selected from the group of glucose oxidase and glucose dehydrogenase.

30. The method of measuring a concentration of an analyte in the subject as claimed in claim 24, wherein the biosensor is connectable to a device body having a control part including a display part and the biosensor further comprises a biosensor insertion signal terminal for interconnecting, upon connecting the biosensor to the device body, two input terminals of the device body to start the control part of the device body.

* * * * *